(12) United States Patent
Elser et al.

(10) Patent No.: US 10,945,776 B2
(45) Date of Patent: Mar. 16, 2021

(54) SURGICAL ASSEMBLY AND METHOD FOR REPAIRING DEPRESSION FRACTURES

(71) Applicant: ARTHREX, INC., Naples, FL (US)

(72) Inventors: Christoph Elser, Moosach (DE);
Niclas W. Schiffer, Munich (DE);
Brandon Roller, Naples, FL (US);
Audrey Chaudot, Munich (DE);
Sebastien Parratte, Marseilles (FR);
Joshua Dines, Southampton, NY (US)

(73) Assignee: Arthrex, Inc., Naples, FL (US)

( * ) Notice: Subject to any disclaimer, the term of this patent is extended or adjusted under 35 U.S.C. 154(b) by 254 days.

(21) Appl. No.: 16/004,984

(22) Filed: Jun. 11, 2018

(65) Prior Publication Data

US 2018/0289409 A1   Oct. 11, 2018

Related U.S. Application Data

(62) Division of application No. 14/691,963, filed on Apr. 21, 2015, now abandoned.

(51) Int. Cl.
*A61B 17/88* (2006.01)
*A61B 17/34* (2006.01)

(52) U.S. Cl.
CPC ...... *A61B 17/8866* (2013.01); *A61B 17/3472* (2013.01); *A61B 17/8811* (2013.01); *A61B 17/8819* (2013.01); *A61B 17/8816* (2013.01); *A61B 2017/3456* (2013.01)

(58) Field of Classification Search
CPC ....................... A61B 17/88–17/8897
See application file for complete search history.

(56) References Cited

U.S. PATENT DOCUMENTS

| | | | | |
|---|---|---|---|---|
| 3,782,381 A | * | 1/1974 | Winnie | A61B 17/3401 604/164.09 |
| 4,756,708 A | * | 7/1988 | Martin | A61B 10/04 600/573 |
| 4,869,718 A | * | 9/1989 | Brader | A61M 16/0465 604/164.04 |
| 6,241,734 B1 | * | 6/2001 | Scribner | A61B 17/8855 606/93 |
| 6,248,110 B1 | * | 6/2001 | Reiley | A61B 17/8811 606/93 |
| 6,692,502 B1 | * | 2/2004 | Ertl | A61B 17/8866 606/86 R |
| 8,415,407 B2 | | 4/2013 | Beyar et al. | |

(Continued)

OTHER PUBLICATIONS

International Search Report and Written Opinion for PCT Application No. PCT/US2015/061212, dated Feb. 4, 2016.

(Continued)

*Primary Examiner* — Zade Coley
(74) *Attorney, Agent, or Firm* — Carlson, Gaskey & Olds, P.C.

(57) ABSTRACT

A surgical method includes accessing a depressed bone fragment of a depression fracture with a surgical assembly. The surgical assembly includes a cannula and an obturator receivable through the cannula. The method further includes positioning the depressed bone fragment toward its original anatomical position using a blunt tip of the obturator. The method also includes injecting a liquid repair material through the cannula to the depression fracture to repair the depression fracture.

14 Claims, 6 Drawing Sheets

(56) References Cited

U.S. PATENT DOCUMENTS

| | | | | |
|---|---|---|---|---|
| 8,852,201 B2* | 10/2014 | Schmieding | ....... | A61B 17/1633 606/80 |
| 2003/0130664 A1* | 7/2003 | Boucher | ............ | A61B 17/8816 606/86 R |
| 2006/0015131 A1* | 1/2006 | Kierce | .................... | A61B 34/73 606/191 |
| 2007/0198024 A1* | 8/2007 | Plishka | .............. | A61B 17/8811 606/93 |
| 2010/0121336 A1* | 5/2010 | Linderman | ........ | A61B 17/8819 606/94 |
| 2010/0160921 A1* | 6/2010 | Sun | ...................... | A61B 17/885 606/92 |
| 2011/0015675 A1* | 1/2011 | Howard | ............. | A61B 17/0469 606/232 |
| 2012/0059380 A1 | 3/2012 | Deangelo et al. | | |
| 2012/0316513 A1* | 12/2012 | Sharkey | .................... | A61F 2/28 604/256 |
| 2013/0006232 A1* | 1/2013 | Pellegrino | .............. | A61B 18/12 606/33 |
| 2014/0257311 A1 | 9/2014 | Druma | | |
| 2014/0358188 A1* | 12/2014 | Larson | ................. | A61B 17/885 606/86 R |

OTHER PUBLICATIONS

International Preliminary Report on Patentability for PCT Application No. PCT/US2015/061212, dated Nov. 2, 2017.

* cited by examiner

SURGICAL ASSEMBLY AND METHOD FOR REPAIRING DEPRESSION FRACTURES

CROSS-REFERENCE TO RELATED APPLICATIONS

This application is a divisional of U.S. patent application Ser. No. 14/691,963, filed Apr. 21, 2015, the disclosure of which is incorporated by reference in its entirety herein.

BACKGROUND

This disclosure relates to a surgical assembly and method for reducing depression fractures.

Prolonged periods of high force impact and stress during sporting activities can result in depression fractures in the articulating surfaces of joints. Collapsed bone fragments associated with the depression fracture can depress into softer cancellous bone located beneath relatively hard cortical bone. The collapsed bone fragments must be returned to their original anatomical position to stabilize the joint and minimize the risk of post traumatic osteoarthritis.

SUMMARY

A surgical assembly according to an exemplary aspect of the present disclosure includes, among other things, a cannula and an obturator receivable through the cannula and configured to manipulate a depressed bone fragment associated with a depression fracture.

In a further non-limiting embodiment of the foregoing surgical assembly, the obturator includes a blunt tip that extends beyond a distal end of the cannula.

In a further non-limiting embodiment of either of the foregoing surgical assemblies, the blunt tip is rounded.

In a further non-limiting embodiment of any of the foregoing surgical assemblies, the blunt tip and the distal end are curved and extend along an axis that is transverse to a longitudinal axis of the surgical assembly.

In a further non-limiting embodiment of any of the foregoing surgical assemblies, the cannula includes a tube that extends between a fitting and a distal end.

In a further non-limiting embodiment of any of the foregoing surgical assemblies, the tube includes a passage that extends between the fitting and the distal end.

In a further non-limiting embodiment of any of the foregoing surgical assemblies, a plurality of openings are formed through the tube at the distal end.

In a further non-limiting embodiment of any of the foregoing surgical assemblies, the obturator includes a shaft that extends between a handle and a blunt tip.

In a further non-limiting embodiment of any of the foregoing surgical assemblies, the handle includes a fitting and a grip that extends from the fitting.

In a further non-limiting embodiment of any of the foregoing surgical assemblies, the obturator is removable from the cannula.

In a further non-limiting embodiment of any of the foregoing surgical assemblies, the assembly includes a delivery device for injecting a repair material through the cannula after removing the obturator.

In a further non-limiting embodiment of any of the foregoing surgical assemblies, the cannula includes a first fitting and the obturator includes a second fitting configured to engage the first fitting to connect the obturator to the cannula.

A surgical method according to another exemplary aspect of the present disclosure includes, among other things, accessing a depressed bone fragment of a depression fracture with a surgical assembly. The surgical assembly includes a cannula and an obturator receivable through the cannula. The method further includes positioning the depressed bone fragment toward its original anatomical position using a blunt tip of the obturator.

In a further non-limiting embodiment of the foregoing surgical method, the accessing step includes locating the blunt tip of the obturator beneath the depressed bone fragment.

In a further non-limiting embodiment of either of the foregoing surgical methods, the locating step includes positioning the blunt tip such that it is generally perpendicular to the depressed bone fragment.

In a further non-limiting embodiment of any of the foregoing surgical methods, the method includes, prior to the accessing step, forming a pilot hole through cortical bone that is located inferior to the depression fracture.

In a further non-limiting embodiment of any of the foregoing surgical methods, the method includes, subsequent to the positioning step, removing the obturator from the cannula.

In a further non-limiting embodiment of any of the foregoing surgical methods, the method includes injecting a repair material through the cannula after the removing step.

In a further non-limiting embodiment of any of the foregoing surgical methods, the blunt tip extends past a distal end of the cannula.

In a further non-limiting embodiment of any of the foregoing surgical methods, the positioning step includes raising the depressed bone fragment toward the original anatomical position.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure details surgical assemblies and associated methods for reducing a depression fracture of a musculoskeletal joint. The surgical assembly includes a cannula and an obturator receivable through the cannula and configured to position a depressed bone fragment. The depressed bone fragment may be accessed and elevated to its original anatomical position using the surgical assembly. These and other features are described in greater detail on the following paragraphs of this detailed description.

Figure 1:
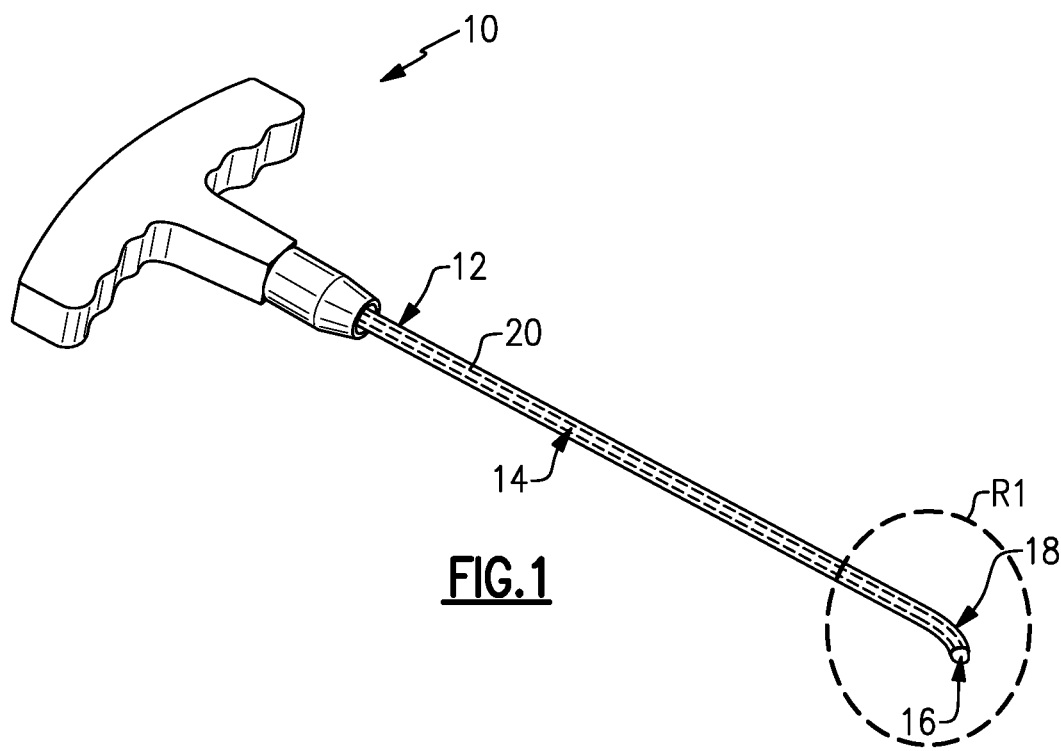
FIG. 1 illustrates a surgical assembly according to a first embodiment of this disclosure.
Figure 2:
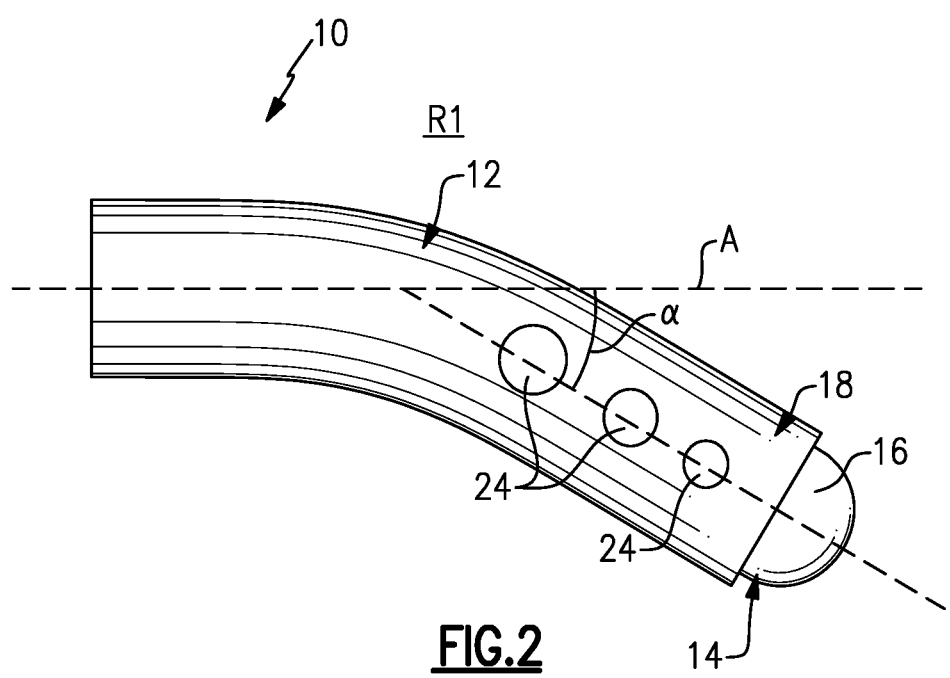
FIG. 2 illustrates a blown up view of region R1 of FIG. 1.

FIGS. 1 and 2 illustrate a surgical assembly 10 for reducing a depression fracture. The surgical assembly 10 includes a cannula 12 and an obturator 14 removably received within the cannula 12. A passage 20 may extend entirely through the cannula 12. In other words, the cannula 12 is cannulated. The obturator 14 is insertable through the passage 20 to access depressed bone fragments associated with a depression fracture. In one non-limiting embodiment, the obturator 14 is removably attachable to the cannula 12. For example, the cannula 12 and obturator 14 may be connected together using a luer connection. Other connections; however, are also contemplated within the scope of this disclosure.

The obturator 14 may include a blunt tip 16 that extends past a distal end 18 of the cannula 12. The blunt tip 16 is configured to position depressed bone fragment(s) associated with a depression fracture. In an embodiment, the blunt tip 16 is configured as a non-traumatic tip designed to avoid damaging the depressed bone fragments.

Referring primarily to FIG. 2, which is a blown up view of region R1 of FIG. 1, both the distal end 18 of the cannula 12 and the blunt tip 16 of the obturator 14 may be curved. In an embodiment, the distal end 18 and the blunt tip 16 are both curved such that they extend at a transverse angle α relative to a longitudinal axis A of the surgical assembly 10. The actual angle of the curvature may vary depending on the joint being repaired, among other factors. The distal end 18 of the cannula 12 and the blunt tip 16 of the obturator 14 may be pre-bent or can be bent in the operating room just prior to performing a depression fracture reduction surgery.

Figure 3:
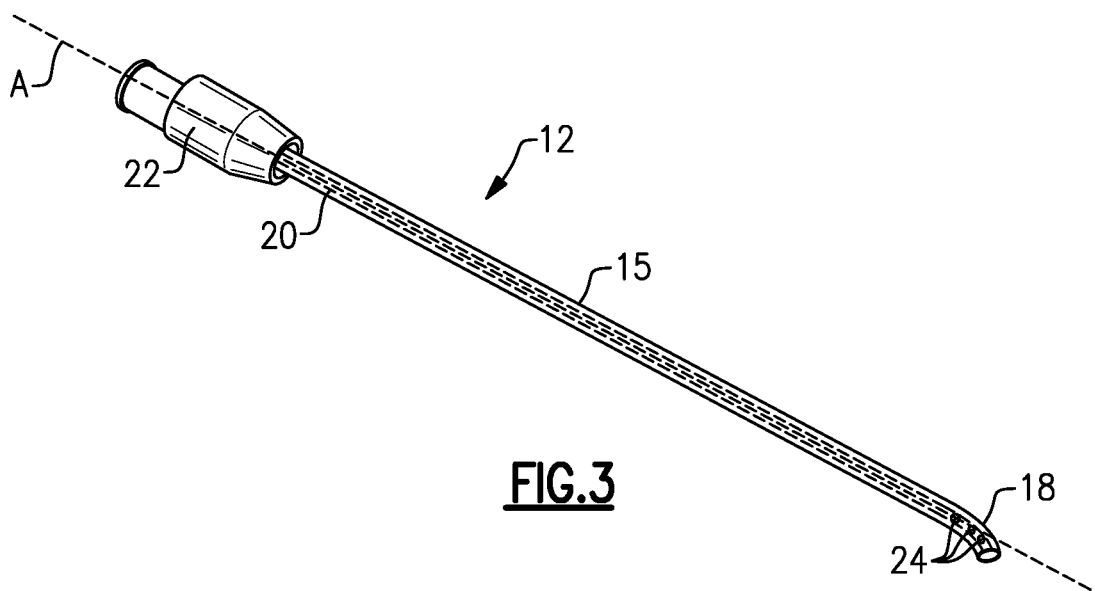
FIG. 3 illustrates a cannula of the surgical assembly of FIG. 1.

FIG. 3, with continued reference to FIGS. 1 and 2, further illustrates the cannula 12 of the surgical assembly 10. The cannula 12 includes a tube 15 that extends along the longitudinal axis A between a fitting 22, disposed proximally, and the distal end 18. The distal end 18 of the cannula 12 may include a plurality of openings 24, or fenestrations, formed through the tube 15. The plurality of openings 24 are in fluid communication with the passage 20 that extends through the tube 15.

Figure 5:
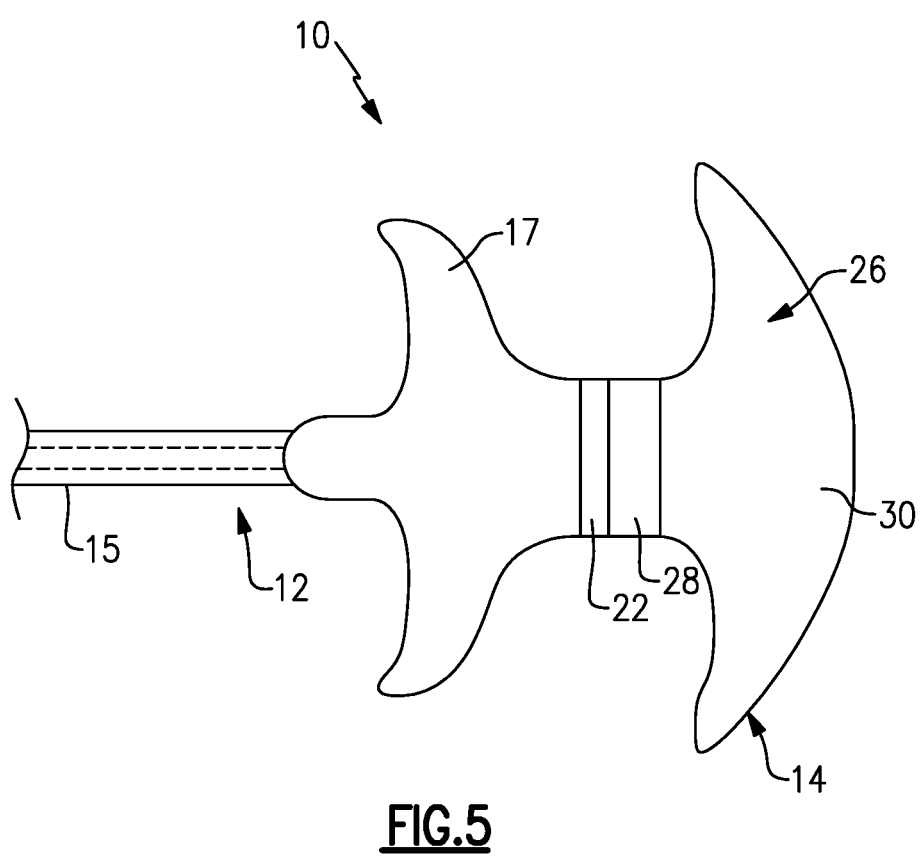
FIG. 5 illustrates portions of a surgical assembly according to another embodiment of this disclosure.

The fitting 22 is configured for connection to the obturator 14. In one non-limiting embodiment, the fitting 22 is a male luer lock fitting that may be rotatably received within a female luer lock fitting of the obturator 14. Other fitting configurations are also contemplated, including an embodiment in which the fitting 22 of the cannula 12 provides the female connection and the obturator 14 provides the male connection. In yet another embodiment, the fitting 22 includes a grip 17 for gripping the cannula 12 (see, for example, the embodiment of FIG. 5).

In one non-limiting embodiment, the cannula 12 is made of a metallic material, such as stainless steel. In another embodiment, the cannula 12 may be made of a non-metallic material, such as a plastic. The tube 15 and the fitting 22 of the cannula 12 may be made of either similar or dissimilar materials.

Figure 4:
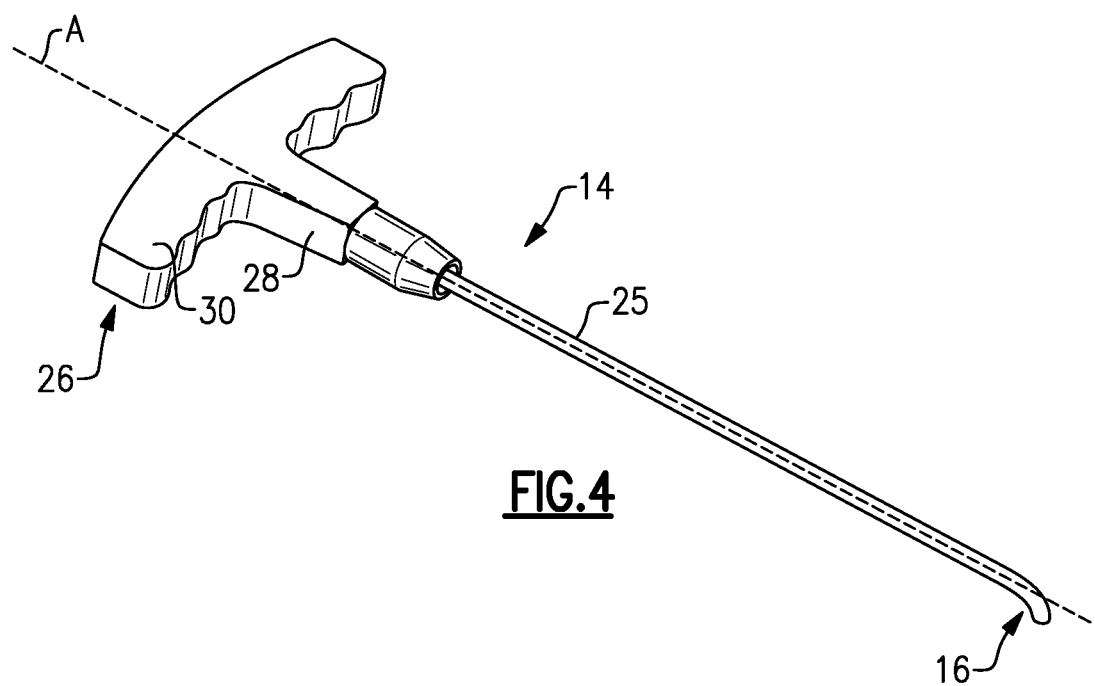
FIG. 4 illustrates an obturator of the surgical assembly of FIG. 1.

FIG. 4, with continued reference to FIGS. 1 and 2, further illustrates the obturator 14 of the surgical assembly 10. The obturator 14 includes a shaft 25 that extends along the longitudinal axis A between a handle 26 and the blunt tip 16. In one non-limiting embodiment, the blunt tip 16 is rounded. However, other non-traumatic shapes are also contemplated within the scope of this disclosure.

The handle 26 may include any size, shape and/or configuration. In other words, the handle 26 is not limited to the specific configurations shown in FIG. 4 or FIG. 5, which illustrate two non-limiting handle configurations. The handle 26 may include a fitting 28 and a grip 30. The fitting 28 is adapted to connect to the fitting 22 of the cannula 12 (see FIGS. 1 and 5) and the grip 30 is configured for gripping the surgical assembly 10.

In one non-limiting embodiment, the obturator 14 is made of a metallic material, such as stainless steel. Other metallic materials may also be suitable. The shaft 25 and the fitting 28 of the obturator 14 may be made of similar or dissimilar materials.

FIGS. 6-10, with continued reference to FIGS. 1-5, schematically illustrate a method for reducing a depression fracture 32 of a joint 34. In one non-limiting embodiment, the joint 34 is a knee joint that includes a femur 36 and a tibia 38 and the depression fracture 32 is a depression fracture of the tibial plateau 40. However, the depression fracture 32 could alternatively be a fracture associated with a Hill Sachs lesion, the calcaneus, the distal radius, or any other bone or joint. In this disclosure, the phrase "depression fracture" indicates a fracture in which one or more bone fragments 45 depress into the softer cancellous bone 42 located beneath relatively hard cortical bone 44. The depressed bone fragment(s) 45 must be returned to their original anatomical position to stabilize the joint 34. The method shown in FIGS. 6-10 may be performed as either an arthroscopic method or an open method.

Figure 6:
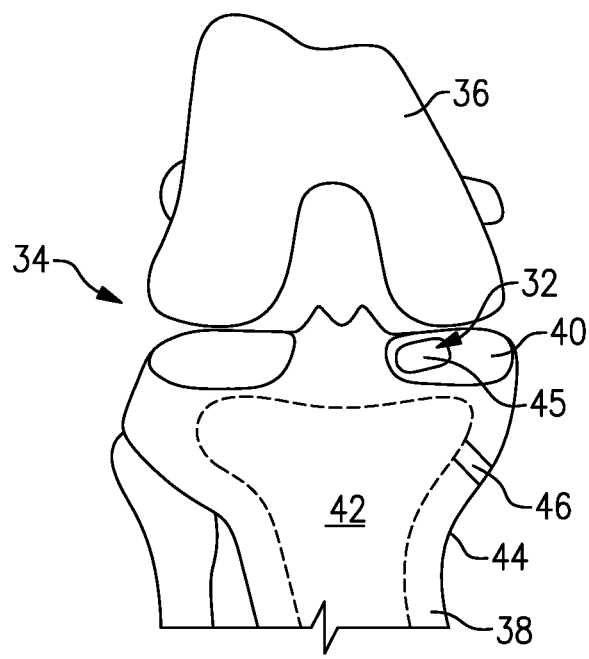
FIGS. 6, 7, 8, 9 and 10 schematically illustrate a method of reducing a depression fracture.

Referring first to FIG. 6, a pilot hole 46 is formed through the cortical bone 44. The pilot hole 46 provides an opening through which the depressed bone fragment(s) 45 associated with the depression fracture 32 may be accessed using the surgical assembly 10. In one non-limiting embodiment, the pilot hole 46 is formed at approximately a 45° angle at a location of the cortical bone 44 that is inferior to (i.e., below) the depression fracture 32. In another embodiment, the pilot hole 46 is formed on the same side of the joint 34 as the depression fracture 32. For example, the pilot hole 46 is formed on the medial side of the tibia 38 if the depression fracture 32 is located medially and is formed on the lateral side of the tibia 38 if the depression fracture 32 is located laterally. The location of the pilot hole 46 may be chosen with the aid of fluoroscopic imaging techniques that provide a real-time understanding of the positioning of the depressed bone fragments 45 and the various other structures that make-up the joint 34.

Figure 7:
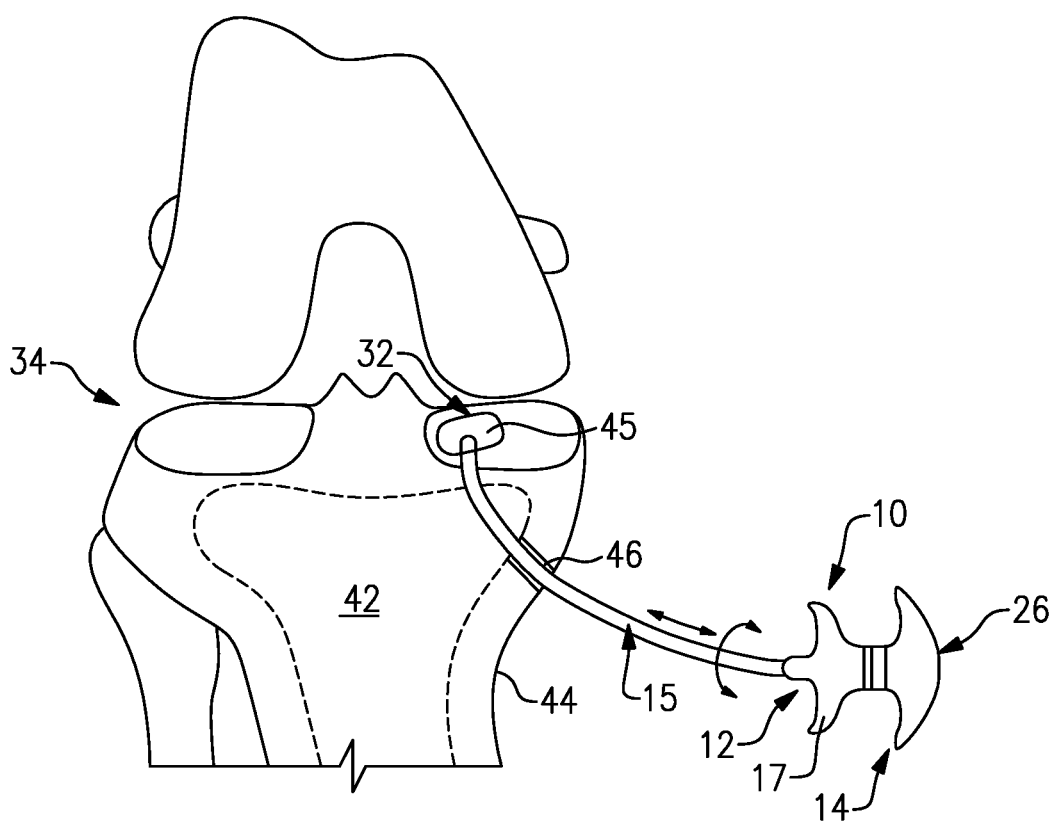

FIG. 7 schematically illustrates guidance of the surgical assembly 10 through the pilot hole 46 for accessing the depressed bone fragment(s) 45. In an embodiment, the tube 15 of the cannula 12 includes an outer diameter that is smaller than the pilot hole 46 to ease insertion of the surgical assembly 10 into the joint 34. The handle 26 of the obturator 14 and/or the grip 17 of the cannula 12 may be used to guide the surgical assembly 10 to a desired positioning beneath the depressed bone fragment(s) 45. The handle 26 and/or the grip 17 also provide sufficient leverage for inserting and guiding the surgical assembly 10 through the cancellous bone 42 to access the depression fracture 32.

Figure 8:
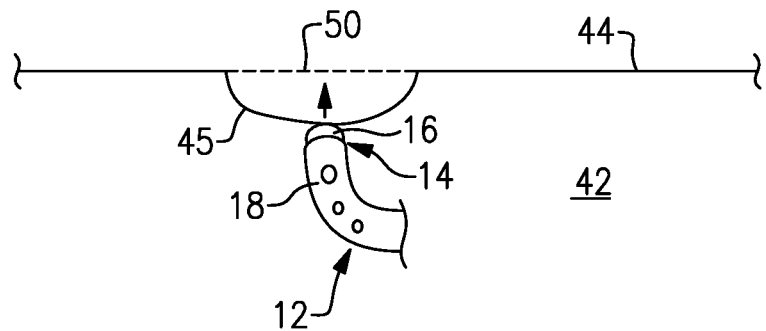

After a desired positioning is achieved, the surgical assembly 10 may be used to manipulate the depressed bone fragment(s) 45 back to an original anatomical positon. For example, as best illustrated in FIG. 8, the blunt tip 16 of the obturator 14 may be used to reduce the depressed bone fragment(s) 45 as close as is possible back to an original anatomical position 50 (shown schematically in dashed lines in FIG. 8). The handle 26 of the obturator 14 and/or the grip 17 of the cannula 12 provide sufficient leverage for lifting the depressed bone fragments 45 of the depression fracture 32. In one non-limiting embodiment, by virtue of the curved nature of the distal end 18 of the cannula 12 and the blunt tip 16 of the obturator 14, the blunt tip 16 may approach the depression fracture 32 at a perpendicular angle relative to the depressed bone fragments 45. Approaching the bone fragments 45 at such an angle simplifies manipulation of the depressed bone fragments 45 for improved approximation back toward the original anatomical position 50.

Figure 9:
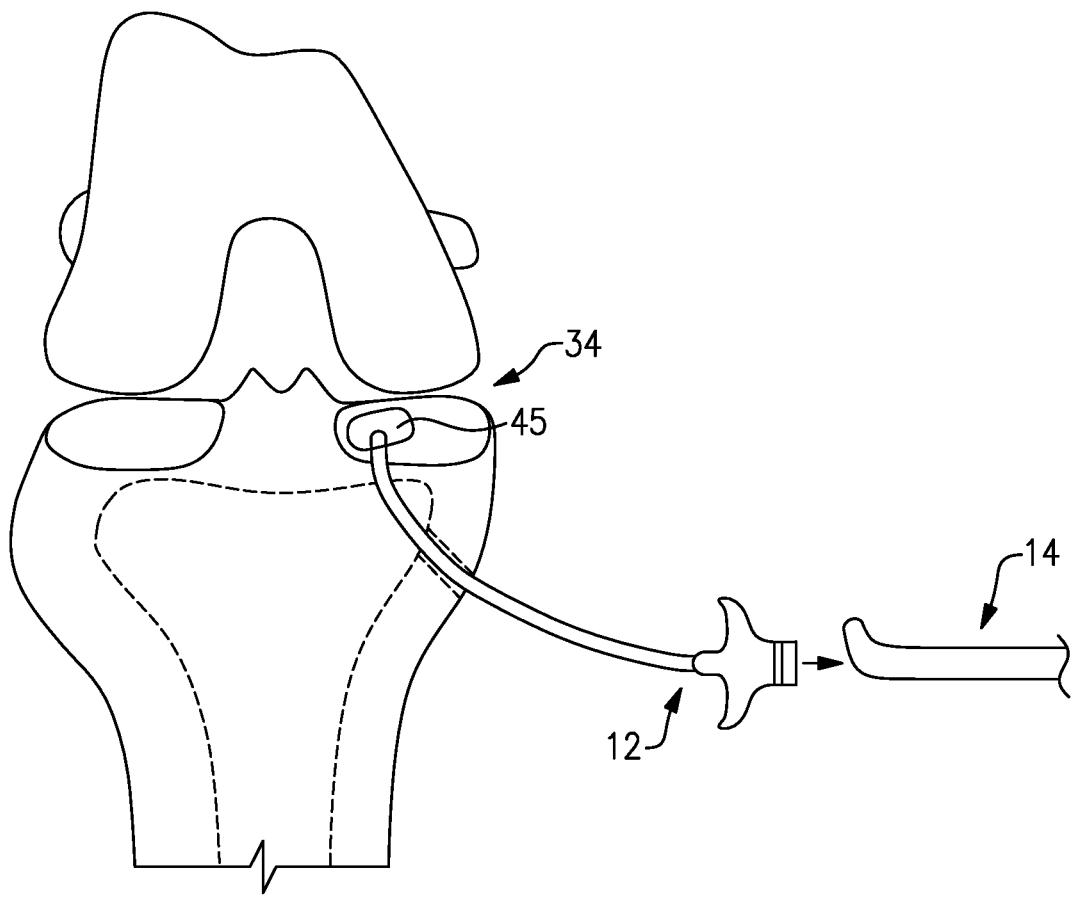

As shown in FIG. 9, the obturator 14 may be disconnected from the cannula 12 and then removed from the joint 34 after reducing the depressed bone fragments 45. The cannula 12, however, may be left inside the joint 34 for preforming additional surgical steps.

Figure 10:
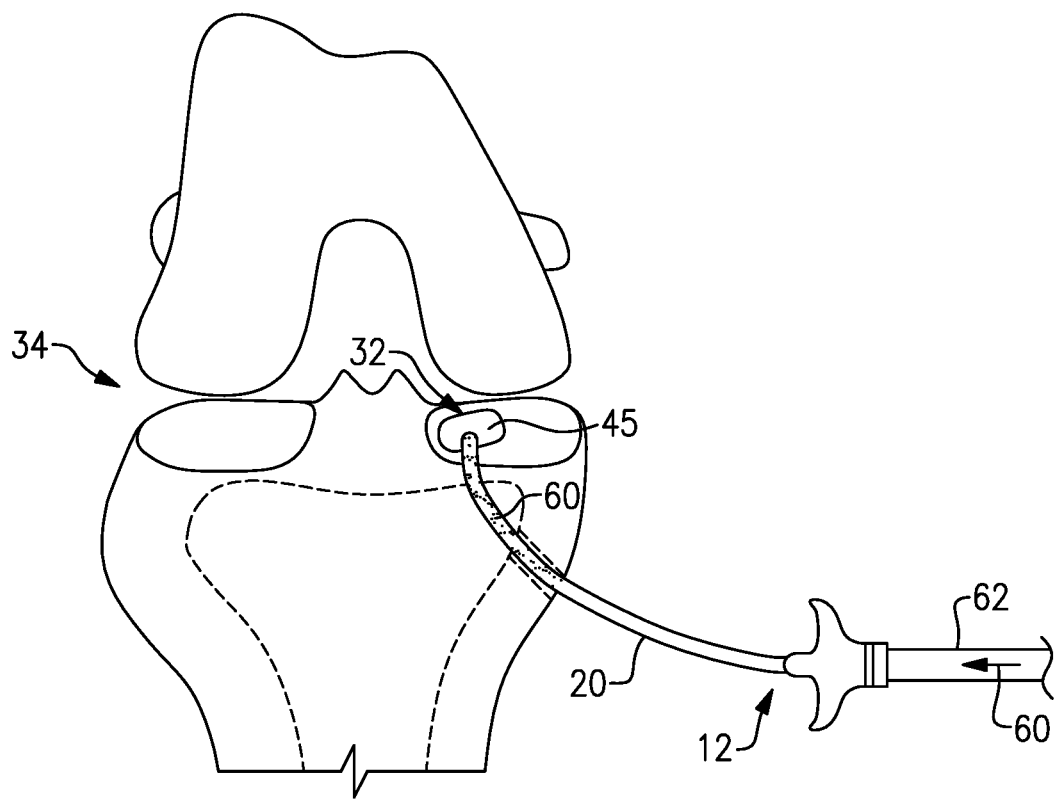

For example, as shown in FIG. 10, a repair material 60 may be injected into the joint 34 to backfill the hollow area immediately beneath the bone fragments 45 of the depression fracture 32, which have not been lifted back toward their original anatomical position. The repair material 60 is delivered using a delivery device 62 that can be inserted into and through the cannula 12. The delivery device 62 may include a syringe and tube, in one non-limiting embodiment. During injection, the repair material 60 may flow through the passage 20 of the cannula 12 and then out of the openings 24 as well as the open distal end 18 (see FIG. 3).

The repair material 60 may include resorbable or non-resorbable bone cement, a bone graft, a bone plug allograft or an autologous material. These, of course, are intended as non-limiting examples of suitable materials. The cannula 12 is removed from the joint 34 to complete the depression fracture reduction procedure.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

The invention claimed is:

1. A surgical method, comprising:
    forming a pilot hole through cortical bone that is located inferior to a depression fracture;
    accessing a depressed bone fragment of the depression fracture with a surgical assembly by locating a blunt tip of an obturator beneath the depressed bone fragment, the surgical assembly including a cannula positioned inside a joint and the obturator receivable through the cannula, wherein the cannula includes a distal end, and the blunt tip of the obturator and the distal end of the cannula are curved and extend along an axis that is transverse to a longitudinal axis of the surgical assembly;
    positioning the depressed bone fragment toward its original anatomical position using the blunt tip of the obturator to raise the depressed bone fragment toward the original anatomical position;
    removing the obturator from the cannula;
    inserting a delivery device in the cannula;
    injecting a liquid repair material through the cannula to the depression fracture with the delivery device to repair the depression fracture; and
    keeping the cannula inside the joint between the steps of removing the obturator from the cannula and injecting the liquid repair material through the cannula.

2. The surgical method as recited in claim 1, comprising removably attaching a first fitting of the cannula to a second fitting of the obturator.

3. The surgical method as recited in claim 1, wherein the injection step includes flowing the liquid repair material through a plurality of openings at the distal end of the cannula.

4. A surgical method, comprising:
    accessing a depressed bone fragment of a depression fracture with a surgical assembly, the surgical assembly including a cannula positioned inside a joint and an obturator receivable through the cannula, wherein the cannula includes a distal end;
    positioning the depressed bone fragment toward its original anatomical position using a blunt tip of the obturator, wherein the blunt tip of the obturator and the distal end of the cannula are curved and extend along an axis that is transverse to a longitudinal axis of the surgical assembly;
    injecting a liquid repair material through the cannula to the depression fracture to repair the depression fracture; and
    keeping the cannula inside the joint between the steps of positioning the depressed bone fragment toward its original anatomical position and injecting the liquid repair material through the cannula.

5. The surgical method as recited in claim 4, wherein the accessing step includes locating the blunt tip of the obturator beneath the depressed bone fragment.

6. The surgical method as recited in claim 5, wherein the locating step includes positioning the blunt tip such that the blunt tip is generally perpendicular to the depressed bone fragment.

7. The surgical method as recited in claim 5, wherein the locating step includes positioning the blunt tip past the distal end of the cannula.

8. The surgical method as recited in claim 4, comprising, prior to the accessing step, forming a pilot hole through cortical bone that is located inferior to the depression fracture.

9. The surgical method as recited in claim 4, comprising, subsequent to the positioning step, removing the obturator from the cannula.

10. The surgical method as recited in claim 4, comprising, prior to the injecting step, inserting a delivery device in the cannula to inject the liquid repair material through the cannula.

11. The surgical method as recited in claim 10, wherein the injecting step includes injecting the liquid repair material through the cannula after the inserting step.

12. The surgical method as recited in claim 4, wherein the positioning step includes raising the depressed bone fragment toward the original anatomical position.

13. The surgical method as recited in claim 4, comprising removably attaching a first fitting of the cannula to a second fitting of the obturator.

14. The surgical method as recited in claim 4, wherein the injection step includes flowing the repair material through a plurality of openings at the distal end of the cannula.

\* \* \* \* \*